(12) United States Patent
Muessig et al.

(10) Patent No.: US 10,441,793 B2
(45) Date of Patent: Oct. 15, 2019

(54) IMPLANTABLE LEADLESS PACEMAKER WITH ATRIAL-VENTRICULAR SYNCHRONIZED PACING

(71) Applicant: BIOTRONIK SE & Co. KG, Berlin (DE)

(72) Inventors: Dirk Muessig, West Linn, OR (US); Andrew B. Kibler, Lake Oswego, OR (US); Larry Stotts, Tigard, OR (US)

(73) Assignee: Biotronik SE & Co. KG, Berlin (DE)

( * ) Notice: Subject to any disclaimer, the term of this patent is extended or adjusted under 35 U.S.C. 154(b) by 41 days.

(21) Appl. No.: 15/631,402

(22) Filed: Jun. 23, 2017

(65) Prior Publication Data

US 2017/0368347 A1 Dec. 28, 2017

Related U.S. Application Data

(60) Provisional application No. 62/354,131, filed on Jun. 24, 2016, provisional application No. 62/354,132, filed on Jun. 24, 2016.

(51) Int. Cl.
*A61N 1/365* (2006.01)
*A61N 1/375* (2006.01)
(Continued)

(52) U.S. Cl.
CPC ........... *A61N 1/3622* (2013.01); *A61N 1/365* (2013.01); *A61N 1/36514* (2013.01); *A61N 1/36578* (2013.01); *A61N 1/3756* (2013.01); *A61N 1/37205* (2013.01); *A61N 1/3682* (2013.01); *A61N 1/3684* (2013.01)

(58) Field of Classification Search
CPC . A61N 1/3622; A61N 1/36578; A61N 1/3756
See application file for complete search history.

(56) References Cited

U.S. PATENT DOCUMENTS

| 2013/0116738 A1* | 5/2013 | Samade | A61N 1/3756 607/3 |
| 2013/0138006 A1* | 5/2013 | Bornzin | A61N 1/3756 600/509 |

(Continued)

OTHER PUBLICATIONS

European Search Report dated Aug. 24, 2017.

*Primary Examiner* — William J Levicky
(74) *Attorney, Agent, or Firm* — Muncy, Geissler, Olds & Lowe, P.C.

(57) ABSTRACT

An implantable leadless pacemaker (iLP) for a human or animal heart, wherein the iLP includes a housing, at least two electrode poles for picking up electrical potentials and/or delivering electrical stimulation, a stimulation control unit in connection with the electrode poles, a sensing unit that is in connection with at least one electrode pole, a signal processing unit in connection with the sensing unit, a signal evaluation unit in connection with the signal processing unit and/or the sensing unit, and an energy source. The sensing unit is configured to sense a first signal associated with an activity of the first heart chamber, and the stimulation control unit is configured to deliver electrical stimulation in the first heart chamber via the at least two electrode poles. wherein the sensing unit is configured to sense a second signal associated with an activity of a second heart chamber.

10 Claims, 7 Drawing Sheets

(51) Int. Cl.
A61N 1/362 (2006.01)
A61N 1/372 (2006.01)
A61N 1/368 (2006.01)

(56) References Cited

U.S. PATENT DOCUMENTS

| | | | |
|---|---|---|---|
| 2014/0107723 A1* | 4/2014 | Hou | A61N 1/3756 |
| | | | 607/28 |
| 2016/0023000 A1* | 1/2016 | Cho | A61N 1/3756 |
| | | | 607/18 |
| 2016/0067490 A1* | 3/2016 | Carney | A61N 1/3756 |
| | | | 607/17 |
| 2016/0129263 A1 | 5/2016 | Demmer et al. | |

\* cited by examiner

IMPLANTABLE LEADLESS PACEMAKER WITH ATRIAL-VENTRICULAR SYNCHRONIZED PACING

This nonprovisional application claims priority to U.S. Provisional Application Nos. 62/354,131 and 62/354,132, which were both filed on Jun. 24, 2016, and which are herein incorporated by reference.

BACKGROUND OF THE INVENTION

Field of the Invention

This invention generally relates to implantable leadless pacemakers (iLP) and methods for operating the same for the purpose of increasing cardiac pacing efficiency and effectiveness.

Description of the Background Art

In the field of implantable leadless pacemakers (iLP), it is desirable to replicate the advanced features found in conventional pacemakers to improve cardiac function and patient well-being. One such feature is that of atrial synchronized ventricular pacing. A dual-chamber leaded pacemaker implanted in a patient with atrial-ventricular block is able to sense atrium events and deliver ventricular paces timed to the atrial events in order to take advantage of atrial preload of the ventricles. In contrast, an iLP implanted in or on the ventricle has no atrial lead, and it is desired that the iLP sense atrial timing such that ventricular paces delivered by it may be appropriately timed to the ventricles' atrial-induced filling period.

In addition, a leadless pacemaker implanted in or on the ventricle has no direct information about any rhythm disorders happening in the atrium (e.g. atrial fibrillation). Providing information about such disorders is of clinical significance as it influences the therapy of the patient.

US 2016/0023000 A1 discloses a leadless pacing device which includes a motion sensor configured to generate a motion signal as a function of heart movement.

US 2016/0067490 A1 discloses a method for adjusting a pacing rate in a dual-chamber, leadless pacemaker implanted in a heart.

It is possible for electrodes placed in proximity to the heart to sense electrical depolarization fields which are generated in tissue which is not immediately adjacent to the electrode. These fields are referred to as far-field signals. In a standard dual-chamber leaded pacemaker device, the strongest far-field signals received are those from the ventricles and are often sensed by the atrial channel. Smaller far-field signals generated in the atrium are sometimes sensed in the ventricular channel. The volume of muscle which contracts in a chamber is directly related to the strength of the far-field signal and as such, far-field sensing of atrial activation is challenging due to the small amount of myocardial tissue of the atrium. The far-field atrial signal is further reduced in a ventricular iLP scenario due to the fact that the iLP senses in bipolar mode (both electrodes in the ventricle) rather than unipolar mode, which typically has stronger far-field signals. Due to these factors and our experience with in-vivo iLP sense signals it is not practical to sense atrial far-field events in the iLP application.

A second known solution makes use of a second device implanted in the atrium. This device may be another iLP, but is practically any device which senses IEGM directly from atrial muscle, and then transmits the information (e.g. sense markers) to the ventricular iLP for the purpose of pacing timing and or statistics. There are several drawbacks to this solution: 1) it requires a secondary device to be implanted in the atrium, a region with sensitive structures and thin walls, increasing system implant time, cost, and risk, 2) it requires frequent device-to-device signaling, which may use significant power, and 3) because the system is not self-contained, the device information should be transmitted in a secure fashion so that a 3rd device is not able to simulate and deliver these markers to the ventricular iLP at incorrect times.

SUMMARY OF THE INVENTION

It is therefore an object of the present invention to solve the problems stated above. It is a further object of the present invention to provide an iLP device which is able to sense atrial activity, synchronize its ventricular pacing to atrial activity, and a system is desired to implement this sensing capability in the iLP device.

According to an exemplary embodiment of the invention, an implantable leadless pacemaker (iLP) for a human or animal heart is disclosed, wherein the iLP comprises: a housing, at least two electrode poles for picking up electrical potentials and/or delivering electrical stimulation, a stimulation control unit in connection with the electrode poles, a sensing unit, wherein the sensing unit is in connection with at least one electrode pole, a signal processing unit in connection with the sensing unit a signal evaluation unit in connection with the signal processing unit and/or the sensing unit, an energy source, wherein the iLP is configured to be anchored within a first heart chamber, and the sensing unit is configured to sense electrical potentials via the at least two electrode poles, wherein the sensing unit is further configured to sense a first signal associated with an activity of the first heart chamber, and the stimulation control unit is configured to deliver electrical stimulation in the first heart chamber via the at least two electrode poles. The sensing unit is configured to sense a second signal associated with an activity of a second heart chamber, wherein the second heart chamber is different from the first heart chamber.

The first heart chamber can be the right ventricle and the second heart chamber can be the right atrium of a human heart, and the iLP according to the invention, having a proximal and distal end, can be anchored in the myocardium of the right ventricle at its distal end. It is also possible that the first heart chamber is the atrium of the heart, such that the iLP is anchored within the myocardium of the atrium, and the second heart chamber is any other chamber of the heart. For anchoring, the iLP comprises at least one fixation member which are located at the distal end, for example, a screw, anchor, tines, hooks, etc.

In an embodiment of the present invention, the iLP comprises telemetry for communication with another device or other devices, as for example other iLPs, subcutaneous implantable cardiac defibrillators (SICD), other forms of implantable and external cardiac pacing and/or monitoring systems, as for instance a cardiac loop recorder. Furthermore, the telemetry can also be applied for communication with external devices programming the iLP or for storing and transmitting device and patient data, for example, devices used within a remote patient monitoring system.

According to an embodiment of the invention, one electrode pole can be located at the distal end of the iLP, in the area of the fixation member. A second electrode can be located at the proximal end of the iLP, or a part of the iLP device housing can for instance serve as counter electrode.

Electrical potentials are picked up via the electrodes and lead to the sensing unit, the signal processing unit and the signal evaluation unit. The electrical potentials are processed in the signal processing unit, as for example using analog and digital signal processing and filtering methods for reducing signal noise, emphasizing parts of the signal for enhanced signal evaluation or the like. The signal evaluation unit evaluates the electrical potentials regarding to cardiac activity. The evaluation can comprise an analysis of the electrogram (ECG) acquired in the first heart chamber. Based on the signal deflections in the ECG, cardiac activity of the first heart chamber and/or the second heart chamber and/or other heart chambers can be derived.

The signal evaluation unit of the iLP according to an embodiment of the invention is configured to detect a first signal characteristic in the first signal, wherein the first signal characteristic indicates a cardiac event of the first heart chamber. For example, the cardiac event of the first heart chamber is the absence of an intrinsic contraction of the first heart chamber. For example, when the first heart chamber is the right ventricle of a heart, the first signal characteristic can be represented by the QRS-complex or R-wave in an ECG. A missing QRS complex in an ECG stands for a missing ventricular contraction, for instance due to an atrioventricular (AV)-block in case atrial contraction is present. In another example, when the first heart chamber is an atrium of a heart, the first signal characteristic can be represented by a P-wave in the ECG.

According to an embodiment of the present invention, the signal evaluation unit can be further configured to detect a second signal characteristic in the second signal, wherein the second signal characteristic indicates a cardiac event of the second heart chamber. For example, the cardiac event of the second heart chamber is the absence or the occurrence of an intrinsic contraction of the second heart chamber. For example, when the second heart chamber is the right atrium of a heart, the second signal characteristic can be represented by the P-wave in an ECG, which stands for atrial contraction. In another example, when the second heart chamber is a ventricle of a heart, the second signal characteristic can be represented by an R-wave in the ECG.

In an embodiment of the disclosed iLP, the stimulation control unit can be configured to deliver electrical stimulation in the first heart chamber in accordance with the cardiac event of the first heart chamber and/or in accordance with the cardiac event of the second heart chamber. By generating electrical stimulation based on the detected events in the first and second heart chamber, it is possible to produce pace therapy based on the information on the contraction state of the paced heart chamber and other heart chambers. As a result, the pacing pulses are applied dependent on intrinsic cardiac activity and cardiac pacing therapy can be applied in a more efficient and effective manner.

The stimulation unit of the iLP according to an embodiment of the invention can be configured to deliver electrical stimulation when a time interval expires after the cardiac event of the second heart chamber has been detected. According to an embodiment of the present invention, the time interval can correspond to a physiological conduction time between the first heart chamber and the second heart chamber. For example, when the first heart chamber is the right ventricle and the second heart chamber the right atrium of the heart, the time interval can be a physiological AV conduction time. The AV conduction time can for instance be predetermined according to corresponding time intervals in the ECG, which is typically the PR interval. PR intervals of a normal heart are in the range of 0.12 to 0.20 seconds.

According to an embodiment of the invention, the time interval can be set according to typical conduction times of a healthy heart. The time interval can also be configured to dynamically adjust to other measured cardiac or physiological parameters, as for example according to the heart rate and changes to the heart rate, the activity level of the patient etc. Furthermore, the time interval according to an embodiment of the invention may be determined according to previous measurements of the intrinsic conduction time of the heart. For example, a series of conduction times can be measured via the iLP (alternatively in dependence of another cardiac or physiological parameter, as for example heart rate or activity level of the patient) and an averaged conduction time calculated via the signal evaluation unit. Such a calculated conduction time can be dynamically calculated and updated in the iLP. Furthermore, according to an embodiment of the invention, electrical stimulation is delivered by the iLP after the time interval has expired and when in this time interval, no intrinsic contraction of the first heart chamber has been sensed. Otherwise, that is in case an intrinsic contraction of the first chamber has occurred during the time interval, the iLP is configured to refrain the delivery of electrical stimulation. The iLP can be configured to deliver electrical stimulation after the expiration of the time interval plus an extra waiting time without sensing an intrinsic contraction of the first heart chamber, wherein the extra waiting time may be set to a fixed time or adjusted dynamically according to other cardiac parameters.

In an embodiment of the disclosed invention, the second signal can be an acoustic and/or a vibration signal representing a heart sound. For example, the sensing unit of the iLP can be an acoustic sensor and/or a vibration sensor. The acoustic and/or vibration sensor are configured to acquire acoustic and/or vibration signals representing cardiac activity. Such signals exhibit, similar to the typical waveforms and time intervals of an ECG, signal features and properties according to the cardiac activity, cardiac state and cardiac cycle. According to an embodiment of the invention, information can be obtained relating to contraction of the heart chambers and events representing such contractions. For example, when the iLP is implanted within the right ventricle of the heart, the acoustic signals and/or vibrations signals acquired via the acoustic and/or vibration sensor may contain signal features representing events for contraction of the ventricle as well as contraction of the atrium, as for example an 'atrial kick'.

In an embodiment of the invention, the second signal can be a mechanical and/or electromechanical signal representing contraction of a heart chamber. For example, the sensing unit of the iLP can comprise a mechanical and/or electromechanical sensor, as for instance a three dimensional (3D) accelerometer. The mechanical and/or electromechanical sensor(s) can be configured to acquire mechanical and/or electromechanical signals representing cardiac activity. Such signals exhibit, similar to the typical waveforms and time intervals of an ECG, signal features and properties according to the cardiac activity, cardiac state and cardiac cycle. According to an embodiment of the invention information can be obtained relating to contraction of the heart chambers and events representing such contractions. For example, when the iLP is implanted within the right ventricle of the heart, the mechanical and/or electromechanical signals acquired via the mechanical and/or electromechanical sensor may contain signal features representing events for contraction of the ventricle as well as contraction of the atrium, as for example an 'atrial kick'.

In an embodiment of the invention, the second signal can be an impedance signal representing a contraction of a heart chamber. For example, the sensing unit of the iLP can comprise an impedance sensor. The impedance sensor can be configured to acquire impedance signals representing cardiac activity. Such signals exhibit, similar to the typical waveforms and time intervals of an ECG, signal features and properties according to the cardiac activity, cardiac state and cardiac cycle. It is proposed according to an embodiment of the invention to obtain information on contraction of the heart chambers and events representing such contractions. For example, when the iLP is implanted within the right ventricle of the heart, the impedance signals acquired via the impedance sensor may contain signal features representing events for contraction of the ventricle as well as contraction of the atrium, as for example an 'atrial kick'.

According to an embodiment of the present invention, the sensing unit of the iLP can comprise at least one sensor, for example, an acoustic sensor, a vibration sensor, a mechanical sensor, an acceleration sensor, an electromechanical sensor, an impedance sensor, a CLS sensor, an ultrasound sensor, a temperature sensor, a pressure sensor, and/or a light sensor.

According to an embodiment of the present invention, the acoustic sensor can be an acoustic transducer installed in the ventricular iLP in combination with an atrial event detection circuit comprised by the signal evaluation unit. The atrial event detection unit processes acoustic signals from the transducer and applies ventricular state timing signals. The iLP sensing unit, stimulation unit, signal processing unit and signal evaluation unit are well suited to detect atrial events and accomplish the stated task. The atrial event detection circuit is able to detect atrio-ventricular filling events from within the ventricle by observing acoustic signals imparted on the device as a result of atrial contraction and blood ejection into the ventricle. This acoustic signal is processed for atrial events according to ventricular state as provided by ventricular event timing signals (sense and pace event markers, blanking) to the atrial event detection circuit.

According to an embodiment of the present invention, the first signal and/or the second signal can be, for example, an electrical signal, a mechanical signal, an electromechanical signal, an ultrasound signal, an impedance signal, a pressure signal, and/or a light signal.

In an embodiment, the first signal and the second signal can be comprised in one composite signal.

The present invention further discloses a method for operating an iLP, the iLP comprising a housing, at least two electrode poles for picking up electrical potentials and/or delivering electrical stimulation, a stimulation control unit in connection with the electrode poles, a sensing unit, wherein the sensing unit is in connection with at least one electrode pole, a signal processing unit in connection with the sensing unit, a signal evaluation unit in connection with the signal processing unit and/or the sensing unit, an energy source, and the method comprises the steps of sensing a first signal associated with an activity of the first heart chamber via the sensing unit, sensing a second signal associated with an activity of a second heart chamber via the sensing unit, wherein the second heart chamber is different from the first heart chamber, and performing electrical stimulation in the first chamber of the heart via the at least two electrode poles via the stimulation control unit.

In an embodiment of the disclosed method, the step of sensing a first signal involves detection of a first signal characteristic in the first signal via the signal evaluation unit, wherein the first signal characteristic indicates a cardiac event of the first heart chamber, and wherein the cardiac event of the first heart chamber is the absence of an intrinsic contraction of the first heart chamber. Preferably, according to an embodiment of the present invention, the step of sensing a second signal involves detection of a second signal characteristic in the second signal via the signal evaluation unit, wherein the second signal characteristic indicates a cardiac event of the second heart chamber, and wherein the cardiac event of the second heart chamber is the absence or the occurrence of an intrinsic contraction of the second heart chamber. Furthermore, according to an embodiment of the present invention, the step of performing electrical stimulation involves starting a timer after the cardiac event of the second heart chamber has been detected and delivering the electrical stimulation in the first heart chamber after expiration of a time interval, wherein the time interval corresponds to a physiological conduction time between two chambers of the heart.

According to an embodiment of the inventive method, the second signal can be an acoustic and/or a vibration signal representing a heart sound. Moreover, the first signal and/or the second signal can be, for example, an electrical signal, a mechanical signal, an electromechanical signal, an ultrasound signal, an impedance signal, a pressure signal, and/or a light signal.

In an embodiment of the present invention, the first signal and the second signal can be comprised in one composite signal.

According to an embodiment of the invention, a system and method for sensing atrial activity via an accelerometer included in an iLP is proposed which provides ventricular pace events preferentially timed to the detected atrial ejection of blood into the ventricles, thus allowing physiologically optimized pacing and utilization of the patients natural rate response to exertion and oxygen demand.

The ventricular iLP can comprise a linear accelerometer in combination with the signal processing unit, for example, with an atrial event detector which processes acceleration signals from the accelerometer and applies ventricular state timing signals from the iLP ventricular sensing unit and stimulation control unit. The atrial event detector is able to detect atrio-ventricular filling events from within the ventricle by observing acceleration imparted on the device as a result of atrial contraction and blood ejection into the ventricle. This acceleration signal is processed for atrial events according to ventricular state as provided by the ventricular event timing signals (sense and pace event markers) to the atrial event detection circuit.

According to an embodiment of the invention, the information of the presence/absence of atrial contraction can be used to detect or confirm atrial tachycardias (e.g. atrial fibrillation). Frequent, irregular atrial events or missing atrial events prior to ventricular events are indicative for the presence of an atrial or A-V nodal arrhythmia as well as the type (atrial flutter vs. atrial fibrillation, vs A-V block). Moreover, the information about the duration of the atrial kick can be used to calculate the optimal AV delay after which the ventricular event needs to occur. It is known that due to intra-/interatrial conduction delays the optimal AV delay is patient specific, and related to the mechanical activation of the atria.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
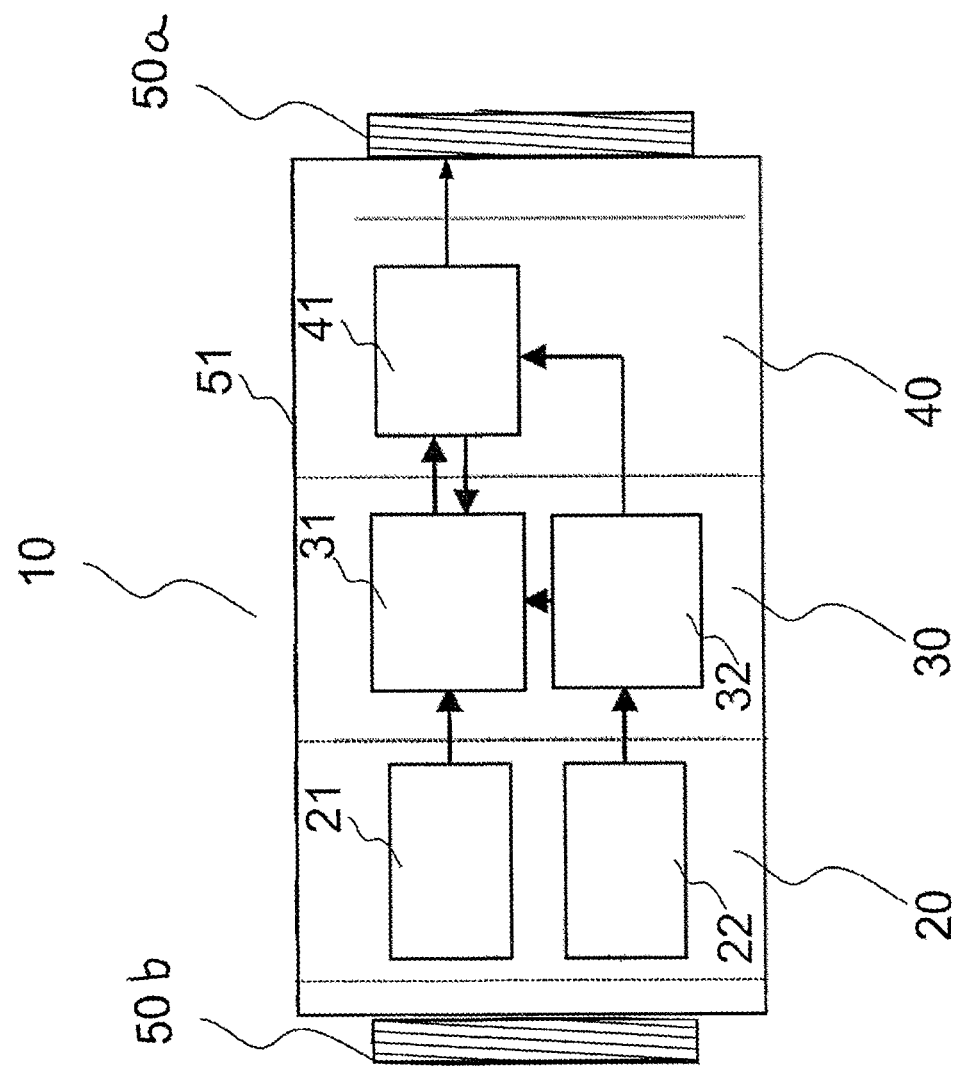
FIG. 1 shows a simplified block diagram of a proposed iLP.

Referring to FIG. 1, an exemplary embodiment of the disclosed iLP 10 according to the invention is depicted schematically. iLP 10 comprises a sensing unit 20, signal processing unit and signal evaluation unit 30, stimulation control unit 40, electrode poles 50a and 50b and housing 51. Sensing unit 20 may include a sensor for detecting a signal which represents atrial activity 21, as for instance an acoustic transducer. Alternatively, sensor 21 may be a vibration sensor, a mechanical sensor, an acceleration sensor, an electromechanical sensor, an impedance sensor, a CLS sensor, an ultrasound sensor, a temperature sensor, a pressure sensor, a light sensor, etc. Signal sensing unit 20 further comprises at least a sensor 22 for measuring an electrogram, for instance a ventricular electrogram. The electrogram may be sensed via electrode poles 50a and 50b. The signal processing unit and signal evaluation unit 30 comprise for instance an atrial event detector 31 and a detector for sensed ventricular events 32, wherein the atrial event detector 31 is configured to detect atrial events in the signal sensed by 21, and the detector for sensed ventricular events 32 is configured to detect ventricular events in the signal sensed by sensor 22. Moreover, signal evaluation unit 30 is configured to relate the detected atrial and ventricular events, such that the atrial event detector 31 processes acoustic signals from the transducer and applies ventricular state timing signals. The atrial event detector 31 is able to detect atrio-ventricular filling events from within the ventricle by observing acoustic signals imparted on the device as a result of atrial contraction and blood ejection into the ventricle. The proposed iLP 10 is capable to detect atrial contraction ('kick') filling events from within the ventricle in which the iLP is implanted. The atrial kick is the ventricular pre-load induced by blood filling the ventricle as the atrium contracts. The action of pre-load causes an acoustic vibration to be induced in the ventricle as the tricuspid valve opens and the ventricle accommodates the incoming blood. This acoustic signal is sensed via an acoustic transducer in the ventricular iLP. The acoustic transducer may be a microphone or any vibrational sensor suitable for the task. The sensed acoustic signal is then processed by the atrial event detector 31 from the signal processing unit 30 which detects atrial events during the quiescent period of ventricular expansion (after the ventricle has contracted, and the tricuspid valve has opened). The atrial event detection circuit monitors this period for sudden atrial-induced acoustic signals which exhibit an acoustic energy beyond a threshold for detection. When an atrial-induced acoustic event is detected, the acoustic signal is processed for atrial events according to ventricular state as provided by ventricular event timing signals (e.g. sense and pace event markers, blanking) to the atrial event detector 31. The atrial event detector 31 may utilize bandpass pre-filtering tuned to the atrial event frequency components, as well as threshold crossing detection on this filtered signal to evaluate the incoming acoustic vibration signal stream for atrial events. Stimulation control unit 40 comprises a pacing control unit 41 which receives information on detected atrial and/or ventricular events from the atrial event detector 31 and the detector for sensed ventricular events 32 and controls electrical stimulation according to the information via electrode 50. Moreover, the information concerning coordination of electrical stimulation can be passed from pacing control unit 41 back to the signal processing unit and the detector for sensed ventricular events 32, and the atrial event detector 31, respectively.

Figure 2:
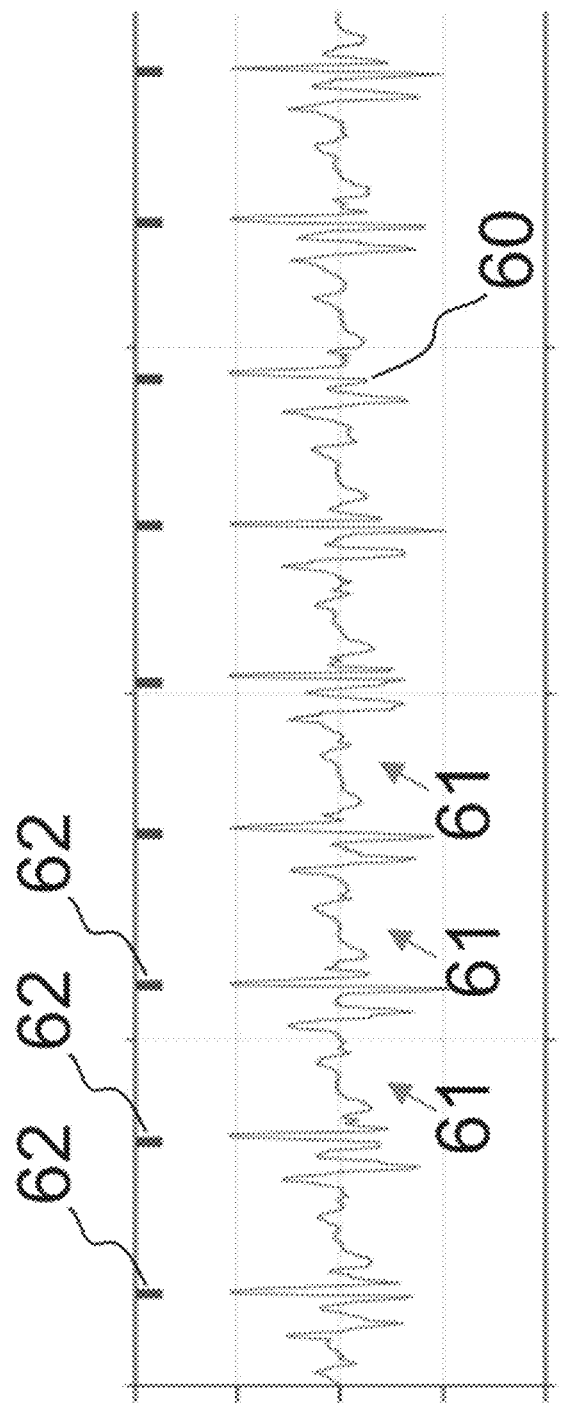
FIG. 2 shows an exemplary set of acoustic sensor data captured in the ventricle showing atrial contraction events.

FIG. 2 shows an example of an acoustic data stream 60 as captured in the ventricle. The atrial contraction events (indicated with arrows 61) immediately prior to ventricular events 62, which are electrically-detected QRS markers sensed in the intracardiac electrogram (IEGM). The information on the ventricular events 62 can be obtained for instance via sensor 22 in combination with sensed ventricular event detector 32, wherein the atrial contraction events 61 can be obtained via sensor 21 in combination with atrial event detector 31. Later heart sounds are induced by systolic phase valve operation, in synchrony with and following the electrical QRS signal.

Figure 3:
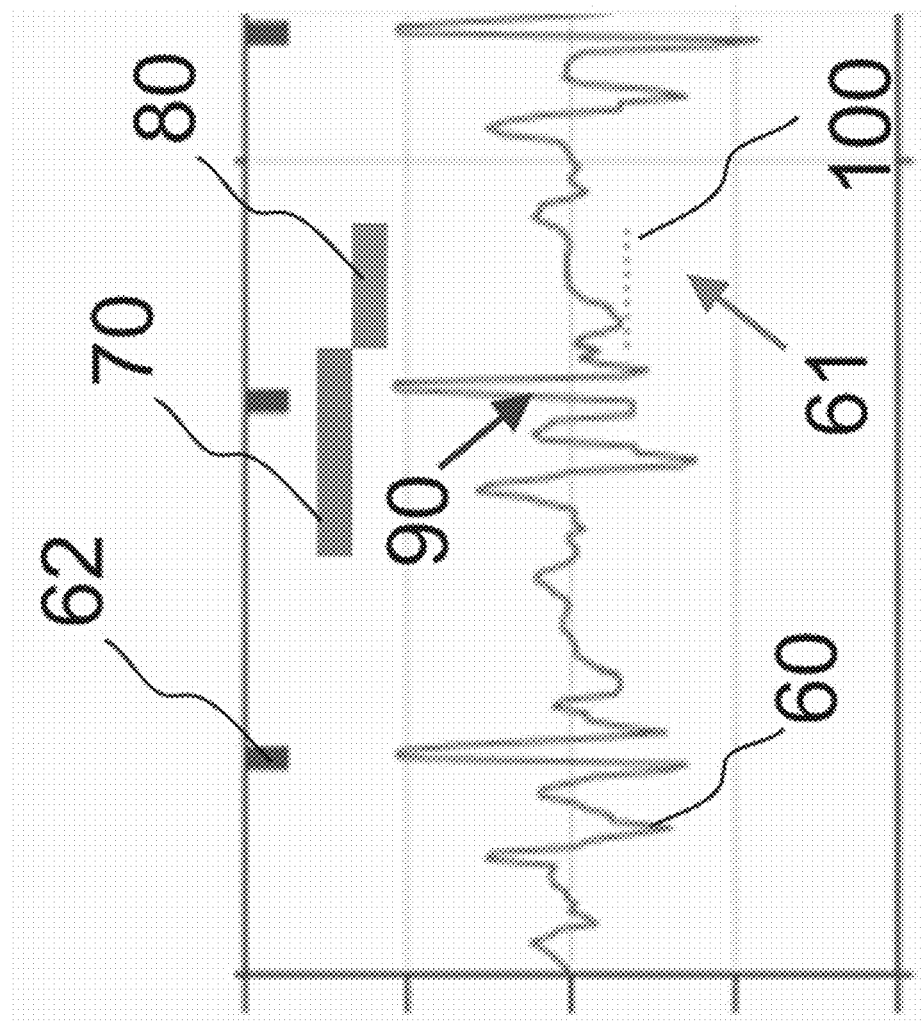
FIG. 3 shows an exemplary set of acoustic sensor data captured in the ventricle with markers indicating cardiac activity.

FIG. 3 shows an exemplary set of acoustic sensor data captured in the ventricle with markers indicating cardiac activity and an example of the inventive method for detecting atrial activity according to an exemplary acoustic data stream 60 as captured in the ventricle electrically-detected QRS markers 62. Following a QRS detection 62, the atrial event detector 31 begins a ventricular systole activity timer 70 during which no atrial activity should be detected. Arrow 90 points to end of a systole as the pulmonary artery valve closes. At the end of ventricular systole phase, the atrial event detector 31 enters a detection phase 80 where the circuit expects an atrial event 61 to trigger its atrial detection marker when the acoustic vibration exceeds a threshold 100. This then counts as an atrial event, which is passed to the iLP signal evaluation unit 30, which may comprise VDD (pacemaker operation mode where electrical stimulation is performed in the ventricle according to atrial activity, involving AV conduction monitoring) timing. For example, in patients exhibiting A-V block arrythmias, atrial event timing as disclosed is used to drive a VDD pacing mode for the iLP. In such an implantable leadless pacemaker, VDD functionality is achieved by use of atrial marker events, which start a ventricular event timer, the expiration of which will cause a ventricular pace if no intrinsic ventricular QRS has been sensed during timer countdown. The benefits of VDD mode vs VVI mode are well known in the cardiac therapeutics field.

Figure 4:
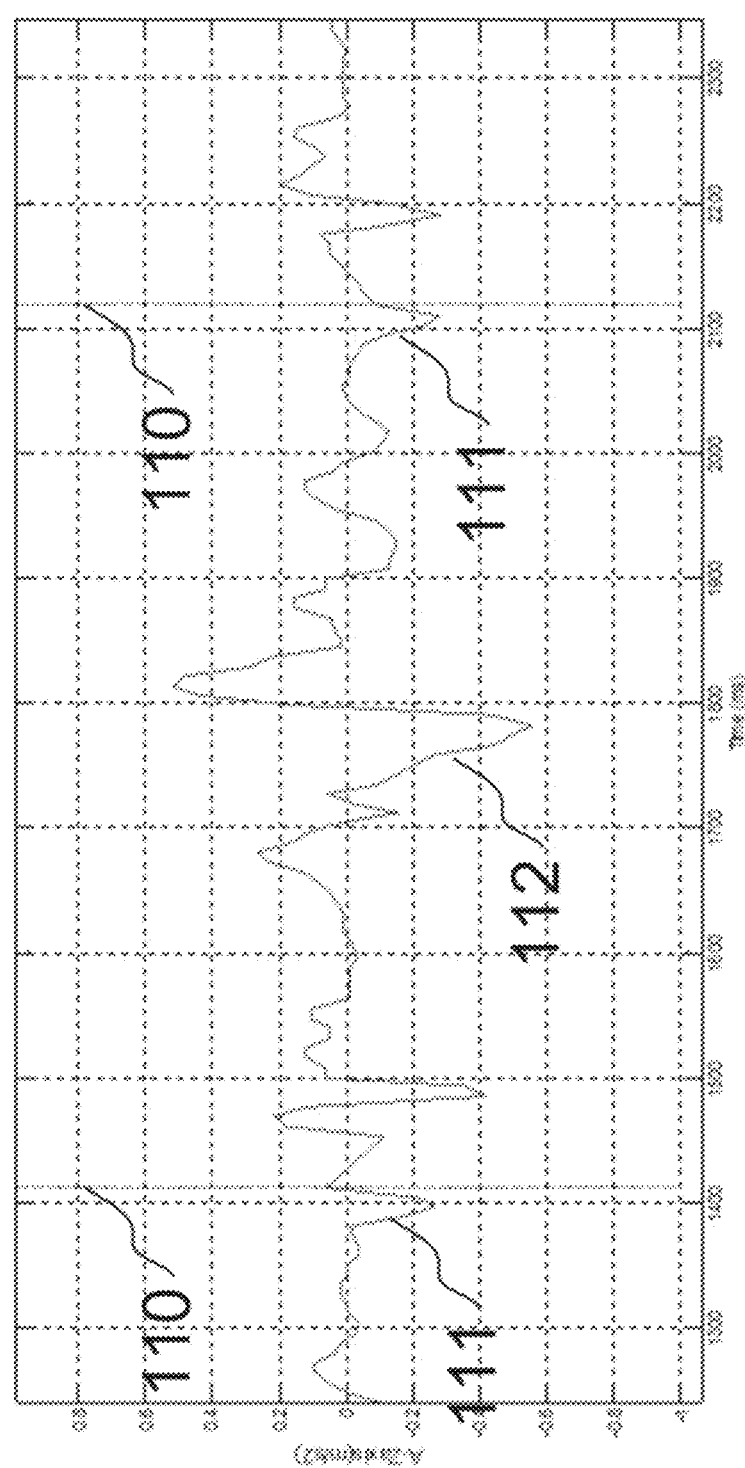
FIG. 4 shows an exemplary set of accelerometer sensor data captured in the ventricle with markers indicating cardiac activity.

FIG. 4 shows an exemplary set of accelerometer data 112 from measurements at the ventricular wall, wherein atrial contraction events 111 can be identified according to the ventricular wall acceleration immediately prior to ventricular IEGM sense events 110. Acceleration later than the ventricular IEGM sense events 110 is due to ventricular contraction and expansion.

Figure 5:
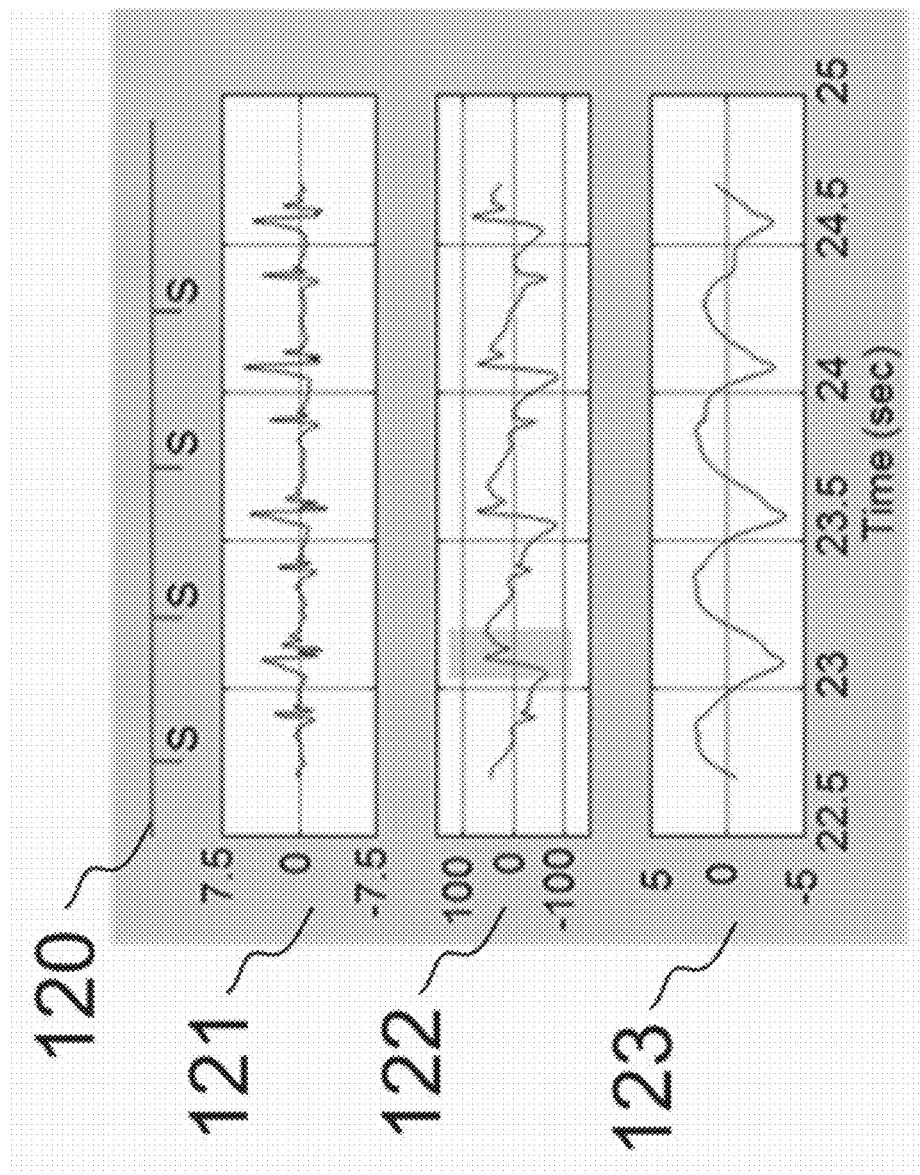
FIG. 5 shows exemplary experimental accelerometer data captured in the ventricle showing atrial contraction events in the ventricular wall acceleration.

In FIG. 5, experimental accelerometer data is illustrated which data calculated from the accelerometer signal measured in the right ventricle wall. 120 is the marker channel corresponding to the right atrium, 121 is the acceleration in m/s$^2$, 122 is the velocity in mm/s, 123 is the displacement in mm. The S in 120 indicates a sensed event in the right atrium, which is an atrial contraction event.

Figure 6:
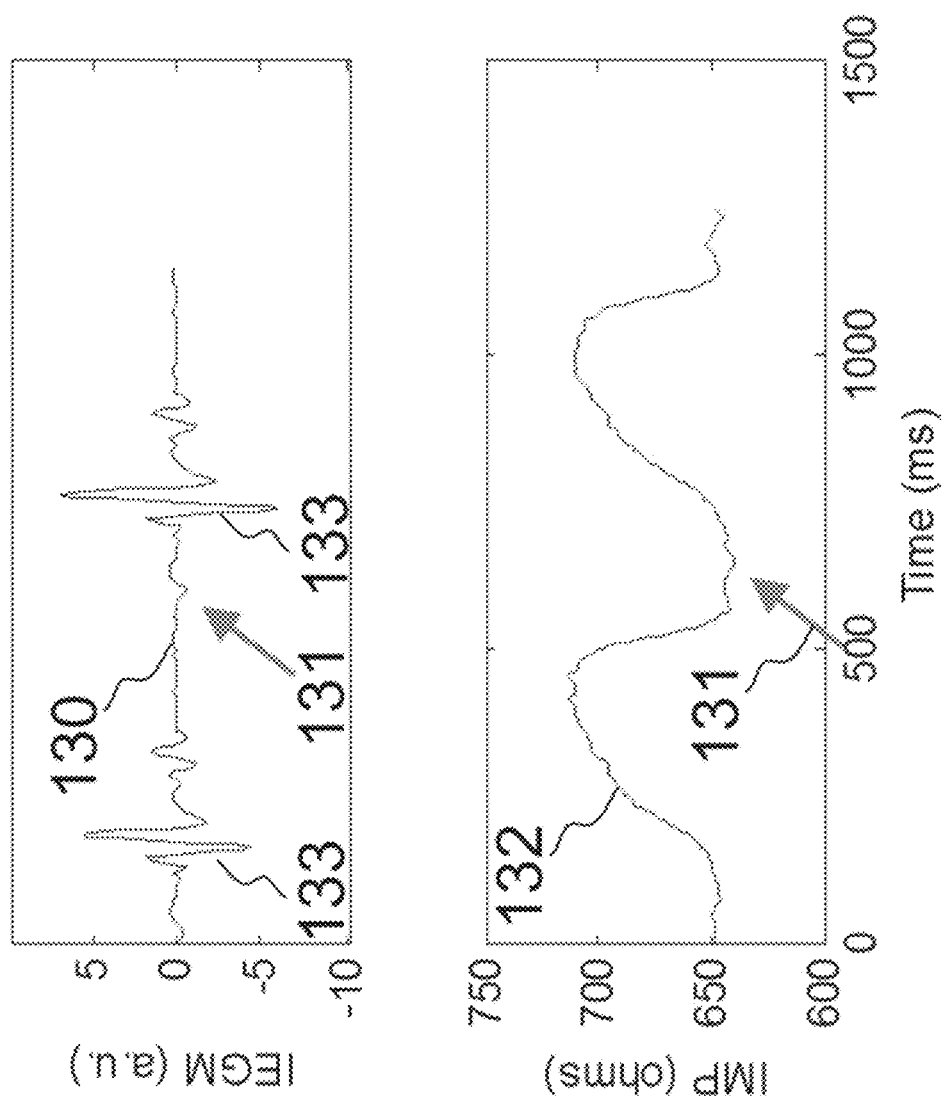
FIG. 6 shows an exemplary set of intracardiac electrogram (IEGM) data and impedance sensor data captured in the ventricle.

FIG. 6 illustrates an experimental IEGM data 130 and the according impedance stream data 132 showing atrial contraction event 131 immediately prior to ventricular IEGM QRS event 133.

Figure 7:
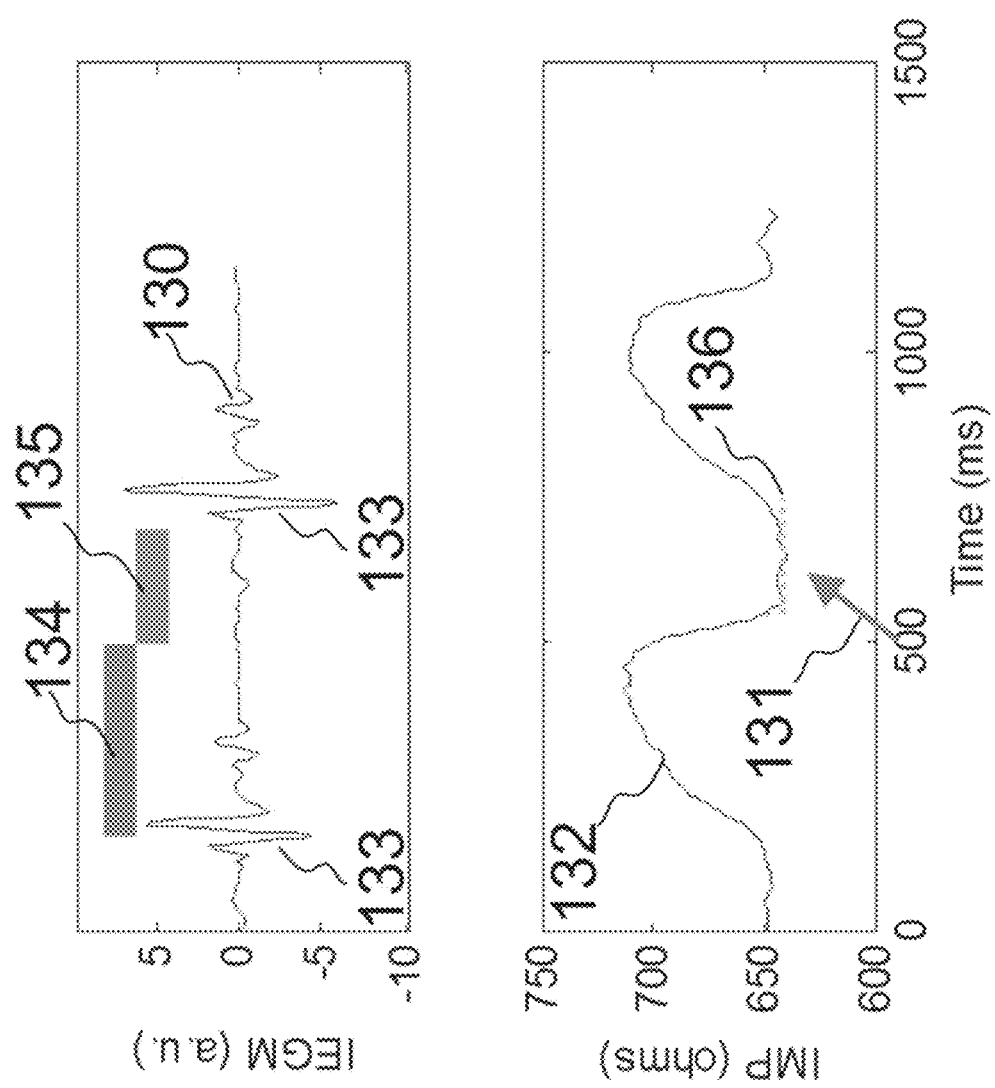
FIG. 7 shows exemplary experimental impedance data captured in the ventricle with markers indicating cardiac activity

FIG. 7 illustrates experimental data from FIG. 6 showing electrical activity markers in the IEGM data 130, and impedance stream data 132 indicating the atrial-induced ventricular impedance deflection. Following a QRS detection 133, the atrial event detector 31 begins a ventricular systole activity timer 134 during which no atrial activity should be detected. At the end of the ventricular systole phase, the atrial event detector 31 enters a detection phase 135 where the circuit expects an atrial event 131 to trigger its atrial detection marker when the impedance exceeds a threshold 136. This then counts as an atrial event, which is passed to the iLP signal evaluation unit 30, which may comprise pacemaker VDD timing and logic circuit.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implantable leadless pacemaker (iLP) for a human or animal heart, the iLP comprising:
    a housing;
    at least two electrode poles for picking up electrical potentials and/or delivering electrical stimulation;
    a stimulation control unit in connection with the electrode poles;
    a sensing unit, wherein the sensing unit is in connection with at least one electrode pole; and
    a signal processing and signal evaluation unit in connection with the sensing unit;
    wherein the iLP is configured to be anchored within a ventricle, and
    wherein the sensing unit is configured to sense electrical potentials via the at least two electrode poles, the sensing unit being configured to sense a first signal associated with an activity of the ventricle,
    wherein the stimulation control unit is configured to deliver electrical stimulation to the ventricle via the at least two electrode poles,
    wherein the sensing unit is configured to sense a second signal,
    wherein the sensing unit comprises an acoustic sensor which is configured to acquire acoustic signals representing cardiac activity,
    wherein the second signal is an acoustic signal which is associated with contraction of an atrium, and
    wherein the signal processing and signal evaluation unit includes an atrial event detector that is configured to detect atrial events in the second signal and wherein the atrial event detector is configured to use bandpass pre-filtering tuned to atrial event frequency components on the second signal to provide a filtered signal and use a threshold crossing detection on the filtered signal, such that the second signal is evaluated for atrial events.

2. The iLP according to claim 1, wherein the signal processing and signal evaluation unit is configured to detect a first signal characteristic in the first signal, the first signal characteristic indicating a cardiac event of the ventricle, and/or wherein the signal processing and signal evaluation unit is configured to detect a second signal characteristic in the second signal, the second signal characteristic indicating a cardiac event of the atrium.

3. The iLP according to claim 2, wherein the cardiac event of the ventricle is an absence of an intrinsic contraction of the ventricle and wherein the cardiac event of the atrium is an absence or occurrence of an intrinsic contraction of the atrium.

4. The iLP according to claim 2, wherein the stimulation control unit is configured to deliver electrical stimulation in the ventricle in accordance with the cardiac event of the ventricle and/or in accordance with the cardiac event of the atrium.

5. The iLP according to claim 2, wherein the stimulation control unit is configured to deliver electrical stimulation when a time interval expires after the cardiac event of the atrium has been detected.

6. The iLP according to claim 5, wherein the time interval corresponds to a physiological conduction time between the ventricle and the atrium.

7. The iLP according to claim 1, wherein the first signal is an electrical signal, a mechanical signal, an electromechanical signal, an ultrasound signal, an impedance signal, an acoustic signal, a vibration signal, a pressure signal, or a light signal.

8. A method for operating an implantable leadless pacemaker (iLP), the iLP comprising:
    a housing;
    at least two electrode poles for picking up electrical potentials and/or delivering electrical stimulation;
    a stimulation control unit in connection with the electrode poles;
    a sensing unit, wherein the sensing unit is in connection with at least one electrode pole; and
    a signal processing and signal evaluation unit in connection with the sensing unit;
    the method comprising:
    sensing a first signal associated with an activity of a ventricle via the sensing unit;
    sensing a second signal via the sensing unit, the sensing unit comprising an acoustic sensor which is configured to acquire acoustic signals representing cardiac activity, such that the second signal is an acoustic signal which is associated with contraction of an atrium; and
    performing electrical stimulation in the ventricle of the heart via the at least two electrode poles via the stimulation control unit, wherein the signal processing and signal evaluation unit includes an atrial event detector that detects atrial events in the second signal by using bandpass pre-filtering tuned to atrial event frequency components on the second signal to provide a filtered signal and uses a threshold crossing detection on the filtered signal, such that the second signal is evaluated for atrial events.

9. The method according to claim 8, wherein the step of sensing a first signal comprises detecting a first signal characteristic in the first signal via the signal processing and signal evaluation unit, the first signal characteristic indicating a cardiac event of the ventricle, the cardiac event of the ventricle being an absence of an intrinsic contraction of the ventricle; and wherein the step of sensing a second signal comprises detecting a second signal characteristic in the second signal via the signal processing and signal evaluation unit, the second signal characteristic indicating a cardiac event of the atrium, and the cardiac event of the atrium being an absence or an occurrence of an intrinsic contraction of the atrium, and wherein the step of performing electrical stimulation comprises starting a timer after the cardiac event of the atrium has been detected and delivering the electrical stimulation in the ventricle after expiration of a time interval, the time interval corresponding to a physiological conduction time between the ventricle and the atrium of the heart.

10. The method according to claim 8, wherein the first signal is an electrical signal, a mechanical signal, an electromechanical signal, an ultrasound signal, an impedance signal, a pressure signal, or a light signal.

\* \* \* \* \*